US008338650B2

(12) United States Patent  (10) Patent No.: US 8,338,650 B2
Johnston et al.  (45) Date of Patent: Dec. 25, 2012

(54) PALLADIUM CATALYSTS FOR MAKING ETHANOL FROM ACETIC ACID

(75) Inventors: Victor J. Johnston, Houston, TX (US); Barbara Kimmich, Bernardsville, NJ (US); John Potts, Angleton, TX (US); Heiko Weiner, Pasadena, TX (US); James H. Zink, League City, TX (US); Josefina T. Chapman, Houston, TX (US); Laiyuan Chen, Houston, TX (US); Radmila Jevtic, Pasadena, TX (US)

(73) Assignee: Celanese International Corporation, Dallas, TX (US)

( * ) Notice: Subject to any disclaimer, the term of this patent is extended or adjusted under 35 U.S.C. 154(b) by 150 days.

(21) Appl. No.: 13/079,700

(22) Filed: Apr. 4, 2011

(65) Prior Publication Data
US 2011/0282110 A1 Nov. 17, 2011

Related U.S. Application Data

(63) Continuation-in-part of application No. 12/698,968, filed on Feb. 2, 2010, and a continuation-in-part of application No. 12/588,727, filed on Oct. 26, 2009, now Pat. No. 8,309,772, which is a continuation-in-part of application No. 12/221,141, filed on Jul. 31, 2008, now Pat. No. 7,863,489.

(51) Int. Cl.
*C07C 29/149* (2006.01)
(52) U.S. Cl. ...................................... 568/885
(58) Field of Classification Search .................... 568/885
See application file for complete search history.

(56) References Cited

U.S. PATENT DOCUMENTS

| 2,021,698 A | 11/1935 | Perkins |
| 2,105,540 A | 1/1938 | Lazier |
| 2,136,704 A | 11/1938 | Mitchell |
| 2,607,807 A | 8/1952 | Ford |
| 2,744,939 A | 5/1956 | Kennel |
| 2,882,244 A | 4/1959 | Milton |
| 3,130,007 A | 4/1964 | Breck |
| 3,478,112 A | 11/1969 | Adam |
| 3,702,886 A | 11/1972 | Araguer |
| 3,729,429 A | 4/1973 | Robson |
| 3,990,952 A | 11/1976 | Katzen |
| 4,065,512 A | 12/1977 | Cares |
| 4,228,307 A | 10/1980 | Zimmerschied |
| 4,270,015 A | 5/1981 | Knifton |
| 4,275,228 A | 6/1981 | Gruffaz |
| 4,317,918 A | 3/1982 | Takano |
| 4,328,373 A | 5/1982 | Strojny |
| 4,337,351 A | 6/1982 | Larkins, Jr. |
| 4,374,265 A | 2/1983 | Larkins, Jr. |
| 4,395,576 A | 7/1983 | Kwantes |
| 4,398,039 A | 8/1983 | Pesa |
| 4,399,305 A | 8/1983 | Schreck |
| 4,421,939 A | 12/1983 | Kiff |
| 4,443,639 A | 4/1984 | Pesa |
| 4,465,854 A | 8/1984 | Pond |
| 4,471,136 A | 9/1984 | Larkins |
| 4,480,115 A | 10/1984 | McGinnis |
| 4,517,391 A | 5/1985 | Schuster |
| 4,521,630 A | 6/1985 | Wattimena |
| 4,550,185 A | 10/1985 | Mabry |
| 4,581,473 A | 4/1986 | Polichnowski |
| 4,613,700 A | 9/1986 | Maki |
| 4,620,050 A | 10/1986 | Cognion |
| 4,678,543 A | 7/1987 | Houben |
| 4,692,218 A | 9/1987 | Houben |
| 4,777,303 A | 10/1988 | Kitson |
| 4,804,791 A | 2/1989 | Kitson |
| 4,826,795 A | 5/1989 | Kitson |
| 4,843,170 A | 6/1989 | Isshiki |
| 4,886,905 A | 12/1989 | Larkins, Jr. |
| 4,902,823 A | 2/1990 | Wunder |
| 4,978,778 A | 12/1990 | Isshiki |
| 4,985,572 A | 1/1991 | Kitson |
| 4,990,655 A | 2/1991 | Kitson |
| 5,008,235 A | 4/1991 | Wegman |
| 5,061,671 A | 10/1991 | Kitson |
| 5,124,004 A | 6/1992 | Grethlein |
| 5,137,861 A | 8/1992 | Shih |
| 5,149,680 A | 9/1992 | Kitson |
| 5,155,084 A | 10/1992 | Horn |
| 5,185,308 A | 2/1993 | Bartley |
| 5,241,106 A | 8/1993 | Inoue |
| 5,243,095 A | 9/1993 | Roberts |
| 5,306,845 A | 4/1994 | Yokohama |
| 5,350,504 A | 9/1994 | Dessau |
| 5,426,246 A | 6/1995 | Nagahara |
| 5,475,144 A | 12/1995 | Watson |
| 5,476,827 A | 12/1995 | Ferrero |
| RE35,377 E | 11/1996 | Steinberg |
| 5,585,523 A | 12/1996 | Weiguny |
| 5,691,267 A | 11/1997 | Nicolau |
| 5,719,315 A | 2/1998 | Tustin |
| 5,731,456 A | 3/1998 | Tustin |
| 5,767,307 A | 6/1998 | Ramprasad |
| 5,821,111 A | 10/1998 | Grady |
| 5,849,657 A | 12/1998 | Rotgerink |
| 5,861,530 A | 1/1999 | Atkins |
| 5,945,570 A | 8/1999 | Arhancet |
| 5,955,397 A | 9/1999 | Didillon |

(Continued)

FOREIGN PATENT DOCUMENTS

EP 0104197 4/1984

(Continued)

OTHER PUBLICATIONS

Alcala, et al., (2005). Experimental and DFT studies of the conversion of ethanol and acetic acid on PtSn-based catalysts, Journal of Physical Chemistry, 109(6), 2074-2085.

(Continued)

*Primary Examiner* — Elvis O Price

(57) ABSTRACT

Catalysts and processes for forming catalysts for use in hydrogenating acetic acid to form ethanol. The catalyst comprises palladium and chromium on a support.

14 Claims, No Drawings

U.S. PATENT DOCUMENTS

| | | | |
|---|---|---|---|
| 5,973,193 A | 10/1999 | Crane |
| 6,040,474 A | 3/2000 | Jobson |
| 6,049,008 A | 4/2000 | Roberts |
| 6,093,845 A | 7/2000 | van Acker |
| 6,114,571 A | 9/2000 | Abel |
| 6,121,498 A | 9/2000 | Tustin |
| 6,232,352 B1 | 5/2001 | Vidalin |
| 6,232,504 B1 | 5/2001 | Barteau |
| 6,294,703 B1 | 9/2001 | Hara |
| 6,462,231 B1 | 10/2002 | Yanagawa |
| 6,472,555 B2 | 10/2002 | Choudary |
| 6,486,366 B1 | 11/2002 | Ostgard |
| 6,495,730 B1 | 12/2002 | Konishi |
| 6,509,180 B1 | 1/2003 | Verser |
| 6,509,290 B1 | 1/2003 | Vaughn |
| 6,559,333 B1 | 5/2003 | Brunelle |
| 6,603,038 B1 | 8/2003 | Hagemeyer |
| 6,632,330 B1 | 10/2003 | Colley |
| 6,657,078 B2 | 12/2003 | Scates |
| 6,685,754 B2 | 2/2004 | Kindig |
| 6,693,213 B1 | 2/2004 | Kolena |
| 6,696,596 B1 | 2/2004 | Herzog |
| 6,727,380 B2 | 4/2004 | Ellis |
| 6,765,110 B2 | 7/2004 | Warner |
| 6,768,021 B2 | 7/2004 | Horan |
| 6,812,372 B2 | 11/2004 | Janssen |
| 6,852,877 B1 | 2/2005 | Zeyss |
| 6,903,045 B2 | 6/2005 | Zoeller |
| 6,906,228 B2 | 6/2005 | Fischer |
| 6,927,048 B2 | 8/2005 | Verser |
| 7,074,603 B2 | 7/2006 | Verser |
| 7,084,312 B1 | 8/2006 | Huber |
| 7,297,236 B1 | 11/2007 | Vander Griend |
| 7,351,559 B2 | 4/2008 | Verser |
| 7,375,049 B2 | 5/2008 | Hayes |
| 7,425,657 B1 | 9/2008 | Elliott |
| 7,507,562 B2 | 3/2009 | Verser |
| 7,518,014 B2 | 4/2009 | Kimmich |
| 7,538,060 B2 | 5/2009 | Barnicki |
| 7,553,397 B1 | 6/2009 | Colley |
| 7,572,353 B1 | 8/2009 | Vander Griend |
| 7,608,744 B1 | 10/2009 | Johnston |
| 7,863,489 B2 | 1/2011 | Johnston |
| 7,884,253 B2 | 2/2011 | Stites |
| 2003/0013908 A1 | 1/2003 | Horan |
| 2003/0077771 A1 | 4/2003 | Verser |
| 2003/0104587 A1 | 6/2003 | Verser |
| 2003/0114719 A1 | 6/2003 | Fischer |
| 2003/0191020 A1 | 10/2003 | Bharadwaj |
| 2004/0195084 A1 | 10/2004 | Hetherington |
| 2006/0019360 A1 | 1/2006 | Verser |
| 2006/0102520 A1 | 5/2006 | Lapinski |
| 2006/0106246 A1 | 5/2006 | Warner |
| 2006/0127999 A1 | 6/2006 | Verser |
| 2007/0270511 A1 | 11/2007 | Melnichuk |
| 2008/0207953 A1 | 8/2008 | Houssin |
| 2009/0005588 A1 | 1/2009 | Hassan |
| 2009/0023192 A1 | 1/2009 | Verser |
| 2009/0081749 A1 | 3/2009 | Verser |
| 2009/0166172 A1 | 7/2009 | Casey |
| 2009/0221725 A1 | 9/2009 | Chornet |
| 2009/0318573 A1 | 12/2009 | Stites |
| 2009/0326080 A1 | 12/2009 | Chornet |
| 2010/0016454 A1 | 1/2010 | Gracey |
| 2010/0029980 A1 | 2/2010 | Johnston |
| 2010/0029995 A1 | 2/2010 | Johnston |
| 2010/0029996 A1 | 2/2010 | Danjo |
| 2010/0030001 A1 | 2/2010 | Chen |
| 2010/0030002 A1 | 2/2010 | Johnston |
| 2010/0113843 A1 | 5/2010 | Lee |
| 2010/0121114 A1 | 5/2010 | Weiner |
| 2010/0168493 A1 | 7/2010 | LePeltier |
| 2010/0196789 A1 | 8/2010 | Fisher |
| 2010/0197485 A1 | 8/2010 | Johnston |
| 2010/0249479 A1 | 9/2010 | Berg-Slot |

FOREIGN PATENT DOCUMENTS

| | | |
|---|---|---|
| EP | 0137749 | 4/1985 |
| EP | 0167300 | 1/1986 |
| EP | 0175558 | 3/1986 |
| EP | 0192587 | 8/1986 |
| EP | 0285420 | 10/1988 |
| EP | 0330853 | 8/1989 |
| EP | 0372847 | 6/1990 |
| EP | 0400904 | 12/1990 |
| EP | 0408528 | 1/1991 |
| EP | 0198682 | 3/1991 |
| EP | 0285786 | 5/1993 |
| EP | 0990638 | 4/2000 |
| EP | 1262234 | 12/2002 |
| EP | 1277826 | 1/2003 |
| EP | 2060553 | 5/2009 |
| EP | 2060555 | 5/2009 |
| EP | 2186787 | 5/2010 |
| GB | 1168785 | 10/1969 |
| GB | 1559540 | 1/1980 |
| GB | 2136704 | 9/1984 |
| JP | 4193304 | 7/1992 |
| JP | 6116182 | 4/1994 |
| JP | 10306047 | 11/1998 |
| JP | 11147845 | 6/1999 |
| JP | 2001046874 | 2/2001 |
| JP | 2001157841 | 6/2001 |
| WO | 8303409 | 10/1983 |
| WO | 03040037 | 5/2003 |
| WO | 2005102513 | 11/2005 |
| WO | 2009009322 | 1/2009 |
| WO | 2009009323 | 1/2009 |
| WO | 2009063176 | 5/2009 |
| WO | 2009086839 | 7/2009 |
| WO | 2009105860 | 9/2009 |
| WO | 2010014145 | 2/2010 |
| WO | 2010014153 | 2/2010 |
| WO | 2010055285 | 5/2010 |

OTHER PUBLICATIONS

Amit M. Goda et al., DFT modeling of selective reduction of acetic acid to acetaldehyde on Pt-based bimetallic catalysts, 20th NAM, Houston, TX, Jun. 17-22, 2007 available online at http://www.nacatsoc.org/20nam/abstracts/O-S9-18.pdf.
Brunauer Emmett and Teller, J. Am. Chem. Soc. 60, 309 (1938).
English langauge abstract for EP 0 137 749 A2.
English langauge abstract for JP 2001-157841 A.
English language abstract for EP 0 192 587 A1.
English language abstract for EP 0 330 853 A2.
English language abstract for JP 10-306047 A.
English language abstract for JP 11-147845 A.
English language abstract for JP 2001-046874 A.
English language abstract for JP 4-193304 A.
English language abstract for JP 6-116182 A.
Gursahani et al., Reaction kinetics measurements and analysis of reaction pathways for conversions of acetic acid, ethanol, and ethyl acetate over silica-supported Pt, Applied Catalysis A: General 222 (2001) 369-392.
International Preliminary Report on Patentability for PCT/US2009/004197 dated Aug. 10, 2010.
International Search Report and Written Opinion for PCT/US2009/004195 mailed Mar. 26, 2010.
International Search Report and Written Opinion for PCT/US2009/004197 mailed Mar. 24, 2010.
Ordonez et al., The role of metal and support sites on the hydrogenation of acetic acid on Ru-based catalysts, 21ST NAM San Francisco, CA, Jun. 10, 2009.
Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.
Pestman et al., (1997). Reactions of Carboxylic Acids on Oxides, Journal of Catalysis 168, 255-264.
Pestman et al., (1998). Identification of the Active Sites in the Selective Hydrogenation of Acetic Acid to Acetaldehyde on Iron Oxide Catalysts, Journal of Catalysis, 174, 142-152.

Pestman et al., The formation of ketones and aldehydes from carboxylic acids, structure-activity relationship for two competitive reactions, Journal of Molecular Catalysis A: Chemical 103 Jun. 14, 1995, 175-180.

Proc. Roy Soc. A314, pp. 473-498 (1970).

Rachmady, Acetic Acid Reduction by H2 on Bimetallic Pt Fe Catalysts, Journal of Catalysis 209, 87-98 (Apr. 1, 2002), Elsevier Science (USA).

Santori et al. (2000). Hydrogenation of carbonylic compounds on Pt/SiO2 catalysts modified with SnBu4, Studies in Surface Science and Catalysis, 130, 2063-2068.

Spivey et al., "Heterogeneous catalytic synthesis of ethanol from biomass-dervied syngas," Chemical Society Review, 2007, vol. 36, pp. 1514-1528.

Subramani et al., "A Review of Recent Literature to Search for an Efficient Catalytic Process for the Conversion of Syngas to Ethanol," Energy & Fuels, 2008, vol. 22, pp. 814-839.

ZeaChem, Inc., Technology Overview, Lakewood, Colorado www.zeachem.com, 2008.

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

PALLADIUM CATALYSTS FOR MAKING ETHANOL FROM ACETIC ACID

CROSS REFERENCE TO RELATED APPLICATIONS

This is a continuation-in-part of U.S. application Ser. No. 12/698,968, filed on Feb. 2, 2010, and a continuation-in-part of U.S. application Ser. No. 12/588,727, filed Oct. 26, 2009, which is a continuation-in-part of U.S. application Ser. No. 12/221,141, filed Jul. 31, 2008, now U.S. Pat. No. 7,863,489, the entireties of which are incorporated herein by reference.

FIELD OF THE INVENTION

The present invention relates generally to catalysts for use in processes for hydrogenating acetic acid to form ethanol, in particular a palladium and chromium catalyst for producing ethanol.

BACKGROUND OF THE INVENTION

There is a long felt need for an economically viable processes and catalysts to convert acetic acid to ethanol which may be used in its own right or subsequently converted to ethylene which is an important commodity feedstock as it can be converted to vinyl acetate and/or ethyl acetate or any of a wide variety of other chemical products. For example, ethylene can also be converted to numerous polymer and monomer products. Fluctuating natural gas and crude oil prices contribute to fluctuations in the cost of conventionally produced, petroleum or natural gas-sourced ethylene, making the need for alternative sources of ethylene all the greater when oil prices rise.

Catalytic processes for reducing alkanoic acids and other carbonyl group containing compounds have been widely studied, and a variety of combinations of catalysts, supports and operating conditions have been mentioned in the literature. The reduction of various carboxylic acids over metal oxides is reviewed by T. Yokoyama et al. in "Fine chemicals through heterogeneous catalysis. Carboxylic acids and derivatives." Chapter 8.3.1, summarizes some of the developmental efforts for hydrogenation catalysts for various carboxylic acids. (Yokoyama, T.; Setoyama, T. "Carboxylic acids and derivatives." in: "Fine chemicals through heterogeneous catalysis." 2001, 370-379.)

A series of studies by M. A. Vannice et al. concern the conversion of acetic acid over a variety of heterogeneous catalysts (Rachmady W.; Vannice, M.A.; J. Catal. (2002) Vol. 207, pg. 317-330.) The vapor-phase reduction of acetic acid by $H_2$ over both supported and unsupported iron was reported in a separate study. (Rachmady, W.; Vannice, M. A. J. Catal. (2002) Vol. 208, pg. 158-169.) Further information on catalyst surface species and organic intermediates is set forth in Rachmady, W.; Vannice, M. A., J. Catal. (2002) Vol. 208, pg. 170-179). Vapor-phase acetic acid hydrogenation was studied further over a family of supported Pt—Fe catalysts in Rachmady, W.; Vannice, M.A. J. Catal. (2002) Vol. 209, pg. 87-98) and Rachmady, W.; Vannice, M. A. J. Catal. (2000) Vol. 192, pg. 322-334).

Various related publications concerning the selective hydrogenation of unsaturated aldehydes may be found in (Djerboua, F.; Benachour, D.; Touroude, R. Applied Catalysis A: General 2005, 282, 123-133.; Liberkova, K.; Tourounde, R. J. Mol. Catal. 2002, 180, 221-230.; Rodrigues, E. L.; Bueno, J. M. C. Applied Catalysis A: General 2004, 257, 210-211.; Ammari, F.; Lamotte, J.; Touroude, R. J. Catal. 2004, 221, 32-42; Ammari, F.; Milone, C.; Touroude, R. J. Catal. 2005, 235, 1-9.; Consonni, M.; Jokic, D.; Murzin, D. Y.; Touroude, R. J. Catal. 1999, 188, 165-175.; Nitta, Y.; Ueno, K.; Imanaka, T.; Applied Catal. 1989, 56, 9-22.)

Studies reporting activity and selectivity over cobalt, platinum and tin-containing catalysts in the selective hydrogenation of crotonaldehyde to the unsaturated alcohol are found in R. Touroude et al. (Djerboua, F.; Benachour, D.; Touroude, R. Applied Catalysis A: General 2005, 282, 123-133 as well as Liberkova, K.; Tourounde, R.; J. Mol. Catal. 2002, 180, 221-230) as well as K. Lazar et al. (Lazar, K; Rhodes, W. D.; Borbath, I.; Hegedues, M.; Margitfalvi, 1. L. Hyperfine Interactions 2002, 139/140, 87-96.)

M. Santiago et al. (Santiago, M. A. N.; Sanchez-Castillo, M. A.; Cortright, R. D.; Dumesic, 1. A. J. Catal. 2000, 193, 16-28.) discuss microcalorimetric, infrared spectroscopic, and reaction kinetics measurements combined with quantum-chemical calculations.

Catalytic activity in for the acetic acid hydrogenation has also been reported for heterogeneous systems with rhenium and ruthenium (Ryashentseva, M. A.; Minachev, K. M.; Buiychev, B. M.; Ishchenko, V. M. Bull. Acad. Sci. USSR 1988, 2436-2439).

U.S. Pat. No. 5,149,680 to Kitson et al. describes a process for the catalytic hydrogenation of carboxylic acids and their anhydrides to alcohols and/or esters utilizing platinum group metal alloy catalysts. U.S. Pat. No. 4,777,303 to Kitson et al. describes a process for the productions of alcohols by the hydrogenation of carboxylic acids. U.S. Pat. No. 4,804,791 to Kitson et al. describes another process for the production of alcohols by the hydrogenation of carboxylic acids. See also U.S. Pat. No. 5,061,671; U.S. Pat. No. 4,990,655; U.S. Pat. No. 4,985,572; and U.S. Pat. No. 4,826,795.

Malinowski et al. (Bull. Soc. Chim. Belg. (1985), 94(2), 93-5), discuss reaction catalysis of acetic acid on low-valent titanium heterogenized on support materials such as silica ($SiO_2$) or titania ($TiO_2$).

Bimetallic ruthenium-tin/silica catalysts have been prepared by reaction of tetrabutyl tin with ruthenium dioxide supported on silica. (Loessard et al., Studies in Surface Science and Catalysis (1989), Volume Date 1988, 48 (Struct. React. Surf), 591-600.)

The catalytic reduction of acetic acid has also been studied in, for instance, Hindermann et al., (Hindermann et al., J. Chem. Res., Synopses (1980), (11), 373), disclosing catalytic reduction of acetic acid on iron and on alkali-promoted iron.

Existing processes suffer from a variety of issues impeding commercial viability including: (i) catalysts without requisite selectivity to ethanol; (ii) catalysts which are possibly prohibitively expensive and/or nonselective for the formation of ethanol and that produce undesirable by-products; and/or (iii) insufficient catalyst life. Thus, the need exists for novel hydrogenation catalysts that have high selectivity, conversion, and productivity to ethanol having catalyst lifetimes that are suitable for commercial hydrogenation processes.

SUMMARY OF THE INVENTION

The present invention is directed to a process for selective and direct formation of ethanol from acetic acid comprising contacting a feed stream comprising acetic acid and hydrogen in vapor form at an elevated temperature with a hydrogenation catalyst comprising palladium and chromium on a catalyst support.

A process for selective and direct formation of ethanol from acetic acid comprising: contacting a feed stream comprising acetic acid and hydrogen in vapor form at an elevated temperature with a hydrogenation catalyst consisting essentially of palladium and chromium on a catalyst support.

DETAILED DESCRIPTION OF THE INVENTION

The present invention relates to processes for producing ethanol by hydrogenating acetic acid in the presence of a catalyst comprising palladium and chromium. The catalyst is a supported catalyst and the support material may comprise silica, titania, iron oxide, zirconium oxide, or alumina. Optionally, the catalyst may further comprise a support modifier. The present invention also relates to processes for making these catalysts.

The hydrogenation of acetic acid to form ethanol may be represented by the following reaction:

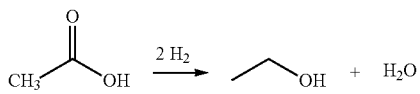

It has surprisingly and unexpectedly been discovered that the catalysts of the present invention provide high selectivities to ethoxylates, such as ethanol and ethyl acetate, and in particular to ethanol, when employed in the hydrogenation of acetic acid. Embodiments of the present invention beneficially may be used in industrial applications to produce ethanol on an economically feasible scale.

Catalyst Metals

The catalyst of the invention comprises palladium and chromium on the support. Preferably, the catalyst does not include any further promoter or secondary metals, such as molybdenum, rhenium, or tungsten. In one embodiment, palladium may be is present in the catalyst in an amount from 0.1 to 10 wt. %, e.g., from 0.4 to 5 wt. %, or from 0.8 to 3 wt. %. The chromium preferably is present in an amount from 0.1 and 20 wt. %, e.g., from 0.5 to 10 wt. %, or from 1 to 5 wt. %. For purposes of the present specification, unless otherwise indicated, weight percent is based on the total weight the catalyst including metal and support. The metal(s) in the catalyst may be present in the form of one or more metal oxides. For purposes of determining the weight percent of the metal(s) in the catalyst, the weight of any oxygen that is bound to the metal is ignored.

The preferred metal ratios may vary, and in some embodiments, the mole ratio of the palladium to chromium preferably is from 10:1 to 1:10, e.g., from 4:1 to 1:4, from 2:1 to 1:2, from 1.5:1 to 1:1.5. At least some of the palladium and chromium may be alloyed with one another or may comprise a non-alloyed metal solution or mixture.

Without being bound by theory, one metal may act as a promoter metal and the other metal is the main metal. For instance, with a palladium and chromium catalyst, palladium may be considered as the main metal and chromium may be considered as the promoter metal. For convenience, the present specification refers to palladium as the main metal and chromium as the promoter. This should not be taken as an indication of the underlying mechanism of the catalytic activity.

Depending primarily on how the catalyst is manufactured, the palladium and chromium of the catalysts of the present invention may be dispersed throughout the support, coated on the outer surface of the support (egg shell) or decorated on the surface of the support.

Support Materials

As will be appreciated by those of ordinary skill in the art, support materials are selected such that the catalyst system is suitably active, selective and robust under the process conditions employed for the formation of ethanol. Suitable support materials may include, for example, stable metal oxide-based supports or ceramic-based supports. Preferred supports include, without limitation, silica, titania, iron oxide, zirconium oxide, alumina, and mixtures thereof.

In one embodiment, the support material is a silicaceous support material selected from the group consisting of silica, silica/alumina, a Group IIA silicate such as calcium metasilicate, pyrogenic silica, high purity silica and mixtures thereof. In the case where silica is used as the silicaceous support, it is beneficial to ensure that the amount of aluminum, which is a common contaminant for silica, is low, preferably under 1 wt. %, e.g., under 0.5 wt. % or under 0.3 wt. %, based on the total weight of the modified support. In this regard, pyrogenic silica is preferred as it commonly is available in purities exceeding 99.7 wt. %. High purity silica, as used throughout the application, refers to silica in which acidic contaminants such as aluminum are present, if at all, at levels of less than 0.3 wt. %, e.g., less than 0.2 wt. % or less than 0.1 wt. %. When calcium metasilicate is used as a support modifier, it is not necessary to be quite as strict about the purity of the silica used as the support material although aluminum remains undesirable and will not normally be added intentionally. The aluminum content of such silica, for example, may be less than 10 wt. %, e.g., less than 5 wt. % or less than 3 wt. %. In cases where the support comprises a support modifier in the range of from 2 wt. % to 10 wt. %, larger amount of acidic impurities, such as aluminum, can be tolerated so long as they are substantially counter-balanced by an appropriate amount of a support modifier.

The surface area of the silicaceous support material, e.g., silica, preferably is at least about 50 m$^2$/g, e.g., at least about 100 m$^2$/g, at least about 150 m$^2$/g, at least about 200 m$^2$/g or most preferably at least about 250 m$^2$/g. In terms of ranges, the silicaceous support material, e.g., silica, preferably has a surface area of from 50 to 600 m$^2$/g, e.g., from 100 to 500 m$^2$/g or from 100 to 300 m$^2$/g. High surface area silica, as used throughout the application, refers to silica having a surface area of at least about 250 m$^2$/g. For purposes of the present specification, surface area refers to BET nitrogen surface area, meaning the surface area as determined by ASTM D6556-04, the entirety of which is incorporated herein by reference.

The silicaceous support material also preferably has an average pore diameter of from 5 to 100 nm, e.g., from 5 to 30 nm, from 5 to 25 nm or from about 5 to 10 nm, as determined by mercury intrusion porosimetry, and an average pore volume of from 0.5 to 2.0 cm$^3$/g, e.g., from 0.7 to 1.5 cm$^3$/g or from about 0.8 to 1.3 cm$^3$/g, as determined by mercury intrusion porosimetry.

The morphology of the support material, and hence of the resulting catalyst composition, may vary widely. In some exemplary embodiments, the morphology of the support material and/or of the catalyst composition may be pellets, extrudates, spheres, spray dried microspheres, rings, pentarings, trilobes, quadrilobes, multi-lobal shapes, or flakes although cylindrical pellets are preferred. Preferably, the silicaceous support material has a morphology that allows for a packing density of from 0.1 to 1.0 g/cm$^3$, e.g., from 0.2 to 0.9 g/cm$^3$ or from 0.5 to 0.8 g/cm$^3$. In terms of size, the silica support material preferably has an average particle size, e.g., meaning the diameter for spherical particles or equivalent spherical diameter for non-spherical particles, of from 0.01 to 1.0 cm, e.g., from 0.1 to 0.5 cm or from 0.2 to 0.4 cm. Since the one or more metal(s) that are disposed on or within the modified support are generally very small in size, they should not substantially impact the size of the overall catalyst particles. Thus, the above particle sizes generally apply to both the size of the modified supports as well as to the final catalyst particles.

A preferred silica support material is SS61138 High Surface Area (HSA) Silica Catalyst Carrier from Saint Gobain Nor Pro. The Saint-Gobain Nor Pro SS61138 silica contains approximately 95 wt. % high surface area silica; a surface area of about 250 m$^2$/g; a median pore diameter of about 12 nm; an average pore volume of about 1.0 cm$^3$/g as measured by mercury intrusion porosimetry and a packing density of about 0.352 g/cm$^3$ (22 lb/ft$^3$).

A preferred silica/alumina support material is KA-160 (Sud Chemie) silica spheres having a nominal diameter of about 5 mm, a density of about 0.562 g/ml, an absorptivity of about 0.583 g H$_2$O/g support, a surface area of about 160 to 175 m$^2$/g, and a pore volume of about 0.68 ml/g.

The total weight of the support, which includes the support material and optional support modifier, based on the total weight of the catalyst, preferably is from 75 wt. % to 99.9 wt. %, e.g., from 78 wt. % to 97 wt. %, or from 80 wt. % to 95 wt. %.

Optional Support Modifiers

Optionally the catalysts of the present invention may also further comprise a modified support, meaning a support that includes a support material and a support modifier, which adjusts the acidity of the support material. In some embodiments, the support comprises a support modifier, such as an acidic or basic modifier, having a low volatility or that is non-volatile. Low volatility modifiers have a rate of loss that is low enough such that the acidity of the support modifier is not reversed during the life of the catalyst.

The optional support modifier preferably is provided in an amount sufficient to adjust the acidity, e.g., by reducing the number or reducing the availability of active Brønsted acid sites for basic support modifiers. In some embodiments, when a basic support modifier is employed to ensure that the surface of the support is substantially free of active Brønsted acid sites. In preferred embodiments, the support modifier is present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst. In preferred embodiments, the support material is present in an amount from 25 wt. % to 99 wt. %, e.g., from 30 wt. % to 97 wt. % or from 35 wt. % to 95 wt. %.

In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Exemplary acidic support modifiers include those selected from the group consisting of TiO$_2$, ZrO$_2$, Nb$_2$O$_5$, Ta$_2$O$_5$, Al$_2$O$_3$, B$_2$O$_3$, P$_2$O$_5$, and Sb$_2$O$_3$. Preferred acidic support modifiers include those selected from the group consisting of TiO$_2$, ZrO$_2$, Nb$_2$O$_5$, Ta$_2$O$_5$, and Al$_2$O$_3$. The acidic modifier may also include WO$_3$, MoO$_3$, Fe$_2$O$_3$, Cr$_2$O$_3$, V$_2$O$_5$, MnO$_2$, CuO, Co$_2$O$_3$, Bi$_2$O$_3$.

Suitable basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used in embodiments of the present invention. Preferably, the support modifier is selected from the group consisting of oxides and metasilicates of any of sodium, potassium, magnesium, calcium, scandium, yttrium, and zinc, and mixtures of any of the foregoing. Preferably, the support modifier is a calcium silicate, more preferably calcium metasilicate (CaSiO$_3$). If the support modifier comprises calcium metasilicate, it is preferred that at least a portion of the calcium metasilicate is in crystalline form.

For example, the acid sites, e.g. Brønsted acid sites, on the support material may be adjusted by the support modifier to favor selectivity to ethanol during the hydrogenation of acetic acid. The acidity of the support material may be adjusted by reducing the number or reducing the availability of Brønsted acid sites on the support material. The support material may also be adjusted by having the support modifier change the pKa of the support material. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference. It has now been discovered that in addition to the metal precursors and preparation conditions employed, metal-support interactions may have a strong impact on selectivity to ethanol. In particular, the use of modified supports that adjust the acidity of the support to make the support less acidic or more basic surprisingly and unexpectedly has now been demonstrated to favor formation of ethanol over other hydrogenation products.

In some embodiments where it is desired for the catalyst to produce ethanol at high selectivity, as indicated above, controlling the Brønsted acidity of the support material by incorporating a support modifier can be quite beneficial. One possible byproduct of the hydrogenation of acetic acid is ethyl acetate. In some embodiments, the support preferably includes a basic support modifier that is effective to suppress production of ethyl acetate, rendering the catalyst composition highly selective to ethanol. Thus, the catalyst composition preferably has a low selectivity toward conversion of acetic acid to ethyl acetate and highly undesirable by-products such as alkanes. The acidity of the support preferably is controlled such that less than 4%, preferably less than 2% and most preferably less than about 1% of the acetic acid is converted to methane, ethane and carbon dioxide. In addition, the acidity of the support may be controlled by using a pyrogenic silica or high purity silica as discussed above.

In one embodiment, the modified support comprises a support material and calcium metasilicate as support modifier in an amount effective to balance Brønsted acid sites resulting, for example, from residual alumina in the silica. Preferably, the calcium metasilicate is present in an amount from 1 wt. % to 10 wt. %, based on the total weight of the catalyst, in order to ensure that the support is essentially neutral or basic in character.

As the basic support modifier, e.g., calcium metasilicate, may tend to have a lower surface area than the support material, e.g., silicaceous support material, in one embodiment the support material comprises a silicaceous support material that includes at least about 80 wt. %, e.g., at least about 85 wt. % or at least about 90 wt. %, high surface area silica in order to counteract this effect of including a support modifier.

Accordingly, without being bound by theory, modification and stabilization of oxidic support materials for the catalysts of the present invention by incorporation of non-volatile support modifiers having either the effect of: counteracting acid sites present upon the support surface or the effect of thermally stabilizing the surface makes it possible to achieve desirable improvements in selectivity to ethanol, prolonged catalyst life, or both. In general, support modifiers based on oxides in their most stable valence state will have low vapor pressures and thus have low volatility or are rather nonvolatile. Accordingly, it is preferred that the support modifiers are provided in amounts sufficient to: (i) counteract acidic sites present on the surface of the support material; (ii) impart resistance to shape change under hydrogenation temperatures; or (iii) both. Without being bound by theory, imparting resistance to shape change refers to imparting resistance, for example, to sintering, grain growth, grain boundary migration, migration of defects and dislocations, plastic deformation and/or other temperature induced changes in microstructure.

Catalyst Preparation

Catalysts of the present invention are particulate catalysts in the sense that, rather than being impregnated in a wash coat onto a monolithic carrier similar to automotive catalysts and diesel soot trap devices, the catalysts of the invention preferably are formed into particles, sometimes also referred to as beads or pellets, having any of a variety of shapes and the catalytic metals are provided to the reaction zone by placing a large number of these shaped catalysts in the reactor. Commonly encountered shapes include extrudates of arbitrary cross-section taking the form of a generalized cylinder in the sense that the generators defining the surface of the extrudate are parallel lines. As indicated above, any convenient particle shape including pellets, extrudates, spheres, spray dried microspheres, rings, pentarings, trilobes, quadrilobes and multi-lobal shapes may be used, although cylindrical pellets are preferred. Typically, the shapes are chosen empirically based upon perceived ability to contact the vapor phase with the catalytic agents effectively.

One advantage of catalysts of the present invention is the stability or activity of the catalyst for producing ethanol. Accordingly, it can be appreciated that the catalysts of the present invention are fully capable of being used in commercial scale industrial applications for hydrogenation of acetic acid, particularly in the production of ethanol. In particular, it is possible to achieve such a degree of stability such that catalyst activity will have rate of productivity decline that is less than 6% per 100 hours of catalyst usage, e.g., less than 3% per 100 hours or less than 1.5% per 100 hours. Preferably, the rate of productivity decline is determined once the catalyst has achieved steady-state conditions.

In one embodiment, when the catalyst support comprises high purity silica, with calcium metasilicate as a basic support modifier, the catalyst activity may extend or stabilize, the productivity and selectivity of the catalyst for prolonged periods extending into over one week, over two weeks, and even months, of commercially viable operation in the presence of acetic acid vapor at temperatures of 125° C. to 350° C. at space velocities of greater than 2500 hr$^{-1}$.

The catalyst compositions of the invention preferably are formed through metal impregnation of the modified support, although other processes such as chemical vapor deposition may also be employed. Before the metals are impregnated, it typically is desired to form the modified support, for example, through a step of impregnating the support material with the support modifier. A precursor to the support modifier, such as an acetate or a nitrate, may be used. In one aspect, the support modifier, e.g., $CaSiO_3$, is added to the support material, e.g., $SiO_2$. For example, an aqueous suspension of the support modifier may be formed by adding the solid support modifier to deionized water, followed by the addition of colloidal support material thereto. The resulting mixture may be stirred and added to additional support material using, for example, incipient wetness techniques in which the support modifier is added to a support material having the same pore volume as the volume of the support modifier solution. Capillary action then draws the support modifier into the pores in the support material. The modified support can then be formed by drying and calcining to drive off water and any volatile components within the support modifier solution and depositing the support modifier on the support material. Drying may occur, for example, at a temperature of from 50° C. to 300° C., e.g., from 100° C. to 200° C. or about 120° C., optionally for a period of from 1 to 24 hours, e.g., from 3 to 15 hours or from 6 to 12 hours. Once formed, the modified supports may be shaped into particles having the desired size distribution, e.g., to form particles having an average particle size in the range of from 0.2 to 0.4 cm. The supports may be extruded, pelletized, tabletized, pressed, crushed or sieved to the desired size distribution. Any of the known methods to shape the support materials into desired size distribution can be employed. Calcining of the shaped modified support may occur, for example, at a temperature of from 250° C. to 800° C., e.g., from 300 to 700° C. or about 500° C., optionally for a period of from 1 to 12 hours, e.g., from 2 to 10 hours, from 4 to 8 hours or about 6 hours.

In a preferred method of preparing the catalyst, the metals are impregnated onto the modified support. A palladium precursor preferably is used in the metal impregnation step, such as a water soluble compound or water dispersible compound/complex that includes the first metal of interest. Depending on the metal precursor employed, the use of a solvent, such as water, glacial acetic acid or an organic solvent, may be preferred. Chromium also preferably is impregnated into the modified support from a chromium precursor.

Impregnation occurs by adding, optionally drop wise, either or both the first metal precursor and/or the second metal precursor and/or additional metal precursors, preferably in suspension or solution, to the dry modified support. The resulting mixture may then be heated, e.g., optionally under vacuum, in order to remove the solvent. Additional drying and calcining may then be performed, optionally with ramped heating to form the final catalyst composition. Upon heating and/or the application of vacuum, the metal(s) of the metal precursor(s) preferably decompose into their elemental (or oxide) form. In some cases, the completion of removal of the liquid carrier, e.g., water, may not take place until the catalyst is placed into use and calcined, e.g., subjected to the high temperatures encountered during operation. During the calcination step, or at least during the initial phase of use of the catalyst, such compounds are converted into a catalytically active form of the metal or a catalytically active oxide thereof.

Impregnation of palladium and chromium into the modified support may occur simultaneously (co-impregnation) or sequentially. In simultaneous impregnation, the palladium and chromium metal precursors are mixed together and added to the modified support together, followed by drying and calcination to form the final catalyst composition. With simultaneous impregnation, it may be desired to employ a dispersion agent, surfactant, or solubilizing agent, e.g., ammonium oxalate, to facilitate the dispersing or solubilizing of the first and second metal precursors in the event the two precursors are incompatible with the desired solvent, e.g., water.

In sequential impregnation, the palladium precursor is first added to the modified support followed by drying and calcining, and the resulting material is then impregnated with the chromium precursor followed by an additional drying and calcining step to form the final catalyst composition. Of course, combinations of sequential and simultaneous impregnation may be employed if desired.

Suitable metal precursors include, for example, metal halides, amine solubilized metal hydroxides, metal nitrates or metal oxalates. For example, suitable compounds palladium precursors include palladium nitrate, palladium tetra ammonium nitrate, palladium chloride, palladium oxalate, and sodium palladium chloride. Exemplary chromium precursors include metal halides, amine solubilized metal hydroxides, metal nitrates or metal oxalates. Generally, both from the point of view of economics and environmental aspects, aqueous solutions of soluble compounds of palladium and chromium are preferred. In one embodiment, the palladium precursor is not a metal halide and is substantially free of metal halides. Without being bound to theory, such non-(metal halide) precursors are believed to increase selectivity to ethanol. A particularly preferred palladium precursor is palladium (II) nitrate and a preferred chromium precursor is chromium (III) nitrate nonahydrate.

In one aspect, the "promoter" metal or metal precursor is first added to the modified support, followed by the "main" or "primary" metal or metal precursor. Of course the reverse order of addition is also possible. As indicated above, in the sequential embodiment, each impregnation step preferably is followed by drying and calcination. In the case of promoted bimetallic catalysts as described above, a sequential impregnation may be used, starting with the addition of the promoter metal followed by a second impregnation step involving co-impregnation of the palladium and chromium metals.

Hydrogenation

The process of hydrogenating acetic acid to form ethanol according to one embodiment of the invention may be conducted in a variety of configurations using a fixed bed reactor or a fluidized bed reactor. In many embodiments of the present invention, an "adiabatic" reactor can be used; that is, there is little or no need for internal plumbing through the reaction zone to add or remove heat. Alternatively, a shell and tube reactor provided with a heat transfer medium can be used. In many cases, the reaction zone may be housed in a single vessel or in a series of vessels with heat exchangers therebetween. It is considered significant that acetic acid reduction processes using the catalysts of the present invention may be carried out in adiabatic reactors as this reactor configuration is typically far less capital intensive than tube and shell configurations.

Typically, the catalyst is employed in a fixed bed reactor, e.g., in the shape of an elongated pipe or tube where the reactants, typically in the vapor form, are passed over or through the catalyst. Other reactors, such as fluid or ebullient bed reactors, can be employed, if desired. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably the reaction is carried out in the vapor phase under the following conditions. The reaction temperature may the range from of 125° C. to 350° C., e.g., from 200° C. to 325° C., from 225° C. to about 300° C., or from 250° C. to about 300° C. The pressure may range from 10 KPa to 3000 KPa (about 0.1 to 30 atmospheres), e.g., from 50 KPa to 2300 KPa, or from 100 KPa to 1500 KPa. The reactants may be fed to the reactor at a gas hourly space velocities (GHSV) of greater than 500 $hr^{-1}$, e.g., greater than 1000 $hr^{-1}$, greater than 2500 $hr^{-1}$ and even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 4:1, e.g., greater than 5:1 or greater than 10:1.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is transferred to the vapor state by passing hydrogen, recycle gas, another suitable gas, or mixtures thereof through the acetic acid at a temperature below the boiling point of acetic acid, thereby humidifying the carrier gas with acetic acid vapors, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syn gas") that is derived from any available carbon source. U.S. Pat. No. 6,232,352, the disclosure of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syn gas is diverted from the methanol synthesis loop and supplied to a separator unit to recover CO and hydrogen, which are then used to produce acetic acid. In a similar manner, hydrogen for the hydrogenation step may be supplied from syn gas.

In some embodiments, some or all of the raw materials for the above-described acetic acid hydrogenation process may be derived partially or entirely from syngas. For example, the acetic acid may be formed from methanol and carbon monoxide, both of which may be derived from syngas. For example, the methanol may be formed by steam reforming syngas, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof.

Methanol carbonylation processes suitable for production of acetic acid are described in U.S. Pat. Nos. 7,208,624, 7,115,772, 7,005,541, 6,657,078, 6,627,770, 6,143,930, 5,599,976, 5,144,068, 5,026,908, 5,001,259, and 4,994,608, the entire disclosures of which are incorporated herein by reference. Optionally, the production of ethanol may be integrated with such methanol carbonylation processes.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syn gas is converted to a methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

Catalyst Conversion and Selectivity

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 200 grams of ethanol per kilogram catalyst per hour, e.g., at least 400 grams of ethanol per kilogram catalyst per hour or at least 600 grams of ethanol per kilogram catalyst per hour, is preferred. In terms of ranges, the productivity preferably is from 200 to 3,000 grams of ethanol per kilogram catalyst per hour, e.g., from 400 to 2,500 per kilogram catalyst per hour or from 600 to 2,000 per kilogram catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 15 tons of ethanol per hour, preferably at least 30 tons of ethanol per hour. In terms of ranges, for large scale industrial production of ethanol, the process of the present invention may produce 15 to 160 tons of ethanol per hour, e.g., 30 to 80 tons of ethanol per hour. Ethanol production from fermentation, due the economies of scale, typically does not permit the single facility ethanol production that may be achievable by employing embodiments of the present invention.

Ethanol Production

In various embodiments of the present invention, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 35 wt. % water. In some embodiments, the crude ethanol product comprises ethanol in an amount from 5 wt. % to 70 wt. %, e.g., from 10 wt. % to 60 wt. %, or from 15 wt. % to 50 wt. %, based on the total weight of the crude ethanol product. Preferably, the crude ethanol product contains at least 10 wt. % ethanol, at least 15 wt. % ethanol or at least 20 wt. % ethanol. The crude ethanol product typically will further comprise unreacted acetic acid, depending on conversion, for example, in an amount of less than 90 wt. %, e.g., less than 80 wt. % or less than 70 wt. %. In terms of ranges, the unreacted acetic acid is preferably from 0 to 90 wt. %, e.g., from 5 to 80 wt. %, from 15 to 70 wt. %, from 20 to 70 wt. % or from 25 to 65 wt. %. As water is formed in the reaction process, water will be present in the crude ethanol product, for example, in amounts ranging from 5 to 35 wt. %, e.g., from 10 to 30 wt. % or from 10 to 26 wt. %.

Ethyl acetate may also be produced during the hydrogenation of acetic acid, or through side reactions and may be present, for example, in amounts ranging from 0 to 20 wt. %, e.g., from 0 to 15 wt. %, from 1 to 12 wt. % or from 3 to 10 wt. %. In addition, acetaldehyde may be produced through side reactions, and may be present, for example, in the crude ethanol product in amounts ranging from 0 to 10 wt. %, e.g., from 0 to 3 wt. %, from 0.1 to 3 wt. % or from 0.2 to 2 wt. %. Other components, such as, for example, esters, ethers, aldehydes, ketones, alkanes, and carbon dioxide, if detectable, collectively may be present in amounts less than 10 wt. %, e.g., less than 6 wt. % or less than 4 wt. %. In terms of ranges, these other components may be present in an amount from 0.1 to 10 wt. %, e.g., from 0.1 to 6 wt. %, or from 0.1 to 4 wt. %. Exemplary component ranges for the crude ethanol product are provided in Table 1.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 10 to 60 | 15 to 50 | 25 to 50 |
| Acetic Acid | 0 to 90 | 5 to 80 | 15 to 70 | 20 to 70 |
| Water | 5 to 35 | 5 to 30 | 10 to 30 | 10 to 26 |
| Ethyl Acetate | 0 to 20 | 0 to 15 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

Ethanol may be recovered from the crude ethanol product using one or more distillation columns. The final ethanol product produced by the process of the present invention may be an industrial grade ethanol comprising from 75 to 96 wt. % ethanol, e.g., from 80 to 96 wt. % or from 85 to 96 wt. % ethanol, based on the total weight of the ethanol product. Exemplary finished ethanol compositional ranges are provided below in Table 2.

TABLE 2

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be higher than indicated in Table 2, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including applications as fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircrafts. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entireties of which are hereby incorporated herein by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

The invention is described in detail below with reference to numerous embodiments for purposes of exemplification and illustration only. Modifications to particular embodiments within the spirit and scope of the present invention, set forth in the appended claims, will be readily apparent to those of skill in the art.

EXAMPLES

In a tubular reactor made of stainless steel, having an internal diameter of 30 mm and capable of being raised to a controlled temperature, a catalyst was arranged comprising 1 wt. % palladium and 5 wt. % chromium on silica. The length of the catalyst bed after charging was approximately 70 mm.

A feed liquid of acetic acid was evaporated and charged to the reactor along with hydrogen and helium as a carrier gas with an average combined gas hourly space velocity (GHSV) of about 2500 $hr^{-1}$ at a temperature of about 250° C. and pressure of 14 barg. The palladium and chromium catalyst demonstrated a selectivity to ethanol of 89.7%. The conversion of acetic acid was 26.3% The selectivity to ethoxylates was 98.9%. The selectivity to ethane was less than 1.1%.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for selective and direct formation of ethanol from acetic acid comprising: contacting a feed stream comprising acetic acid and hydrogen in vapor form at an elevated temperature with a hydrogenation catalyst comprising palladium and chromium on a catalyst support.

2. The process of claim 1, wherein the catalyst support is selected from the group consisting of silica, titania, iron oxide, zirconium oxide, alumina, and mixtures thereof.

3. The process of claim 1, wherein the loading of palladium is from 0.1 wt. % to 10 wt. %.

4. The process of claim 1, wherein the loading of the chromium is from 0.1 wt. % to 20 wt. %.

5. The process of claim 1, wherein the loading of palladium is from 0.4 to 5 wt. % and the loading of chromium is from 0.5 to 10 wt. %.

6. The process of claim 1, wherein the process yields an acetic acid conversion of at least 10%.

7. The process of claim 1, wherein the hydrogenation catalyst has a selectivity to ethanol of at least 40%.

8. The process of claim 1, wherein the hydrogenation catalyst has a selectivity to methane, ethane, and carbon dioxide of less than 4%.

9. The process of claim 1, wherein the hydrogenation catalyst has a selectivity to ethoxylates of at least 40%.

10. The process of claim 1, wherein the hydrogenation of acetic acid is carried out at a temperature of 125° C. to 350° C.

11. The process of claim 1, wherein the hydrogenation of acetic acid is carried out at a pressure of 10 KPa to 3000 KPa.

12. The process of claim 1, wherein the hydrogenation catalyst further comprises a support modifier.

13. The process of claim 1, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

14. A process for selective and direct formation of ethanol from acetic acid comprising: contacting a feed stream comprising acetic acid and hydrogen in vapor form at an elevated temperature with a hydrogenation catalyst consisting essentially of palladium and chromium on a catalyst support.

* * * * *